United States Patent [19]

Chappuis

[11] Patent Number: 5,769,781
[45] Date of Patent: Jun. 23, 1998

[54] PROTECTOR RETRACTOR

[76] Inventor: James L. Chappuis, 3170 Lake Ridge Dr., Marietta, Ga. 30067

[21] Appl. No.: 556,594

[22] Filed: Nov. 13, 1995

[51] Int. Cl.⁶ .................................................. A61B 11/02
[52] U.S. Cl. ..................... 600/202; 600/201; 600/210; 600/226; 600/235
[58] Field of Search .................................. 600/201, 202, 600/210, 213, 217, 226, 235; 606/102; 128/774, 777

[56] References Cited

U.S. PATENT DOCUMENTS

| | | | |
|---|---|---|---|
| 2,677,369 | 5/1954 | Knowles | 128/92 |
| 3,228,393 | 1/1966 | Michele | 128/92 |
| 3,426,364 | 2/1969 | Lumb | 3/1 |
| 3,848,601 | 11/1974 | Ma et al. | 128/305 |
| 3,855,638 | 12/1974 | Pilliar | 3/1 |
| 3,867,728 | 2/1975 | Stubstad et al. | 3/1 |
| 3,871,031 | 3/1975 | Boutin | 3/1 |
| 3,893,196 | 7/1975 | Hochman | 3/1.91 |
| 4,206,516 | 6/1980 | Pilliar | 3/1.9 |
| 4,309,777 | 1/1982 | Patil | 3/1.91 |
| 4,349,921 | 9/1982 | Kuntz | 3/1 |
| 4,550,448 | 11/1985 | Kenna | 623/16 |
| 4,553,273 | 11/1985 | Wu | 623/18 |
| 4,566,466 | 1/1986 | Ripple et al. | 128/781 |
| 4,599,086 | 7/1986 | Doty | 623/17 |
| 4,714,469 | 12/1987 | Kenna | 623/17 |
| 4,739,750 | 4/1988 | Masse et al. | 128/92 |
| 4,743,256 | 5/1988 | Brantigan | 623/17 |
| 4,743,258 | 5/1988 | Ikada et al. | 623/1 |
| 4,759,766 | 7/1988 | Buettner-Janz et al. | 623/17 |
| 4,784,150 | 11/1988 | Voorhies et al. | 128/664 |
| 4,834,757 | 5/1989 | Brantigan | 623/17 |
| 4,878,915 | 11/1989 | Brantigan | 623/17 |
| 4,921,493 | 5/1990 | Webb, Jr. et al. | 606/85 |
| 4,936,848 | 6/1990 | Bagby | 623/17 |
| 4,950,296 | 8/1990 | McIntyre | 623/16 |
| 4,961,740 | 10/1990 | Ray et al. | 606/61 |
| 4,997,432 | 3/1991 | Keller | 606/61 |
| 5,123,403 | 6/1992 | Lavyne | 128/20 |
| 5,135,528 | 8/1992 | Winston | 606/79 |
| 5,192,327 | 3/1993 | Brantigan | 623/17 |
| 5,306,307 | 4/1994 | Senter et al. | 623/17 |
| 5,306,309 | 4/1994 | Wagner et al. | 623/17 |

OTHER PUBLICATIONS

Piezoelectric Copolymer Hydrophone Tile (Hydrostatic Mode), AMP, 114–1082, Nov. 29, 1994.

General Impact Sensor (GPI), AMP, 408–9943, Aug. 1, 1993.

Anterior Discectomy and Interbody Fusion for Lumbar Disc Herniation, Inoue et al., Oct., 1995–Dec., 1982.

Interbody Lumbar Fusion Using a Carbon Fiber Cage Implant Versus Allograft Bone, Brantigan et al., SPINE vol. 19, No. 13, pp. 1436–1444, 1994, J.B. Lippincott Co.

Clinical Orthopaedics and Related Research, No. 193, CORTBR–ISSN 0009–921X, Mar. 1985.

*Primary Examiner*—Beverly M. Flanagan
*Attorney, Agent, or Firm*—Isaf, Vaughan & Kerr

[57] ABSTRACT

A handle carries a dry cell battery which supplies current to a microprocessor which receives signals from a sensor on the end of a bill carried by a staff which projects from the handle. The signal to the microprocessor is converted to a display on the handle. The display has alarms to indicate when the retractor applies too much force to a spinal cord or when the force has been applied for too long a time.

20 Claims, 6 Drawing Sheets

PROTECTOR RETRACTOR

FIELD OF THE INVENTION

The present invention relates generally to surgical retractors and more particularly relates to a surgical protector retractor and process for retracting and protracting body tissue, such as a spinal cord, and monitoring the pressure applied to the tissue and displaying such information to the user.

BACKGROUND OF THE INVENTION

A retractor is an instrument used during surgery for drawing aside the edges of a wound or for holding back structures adjacent to the operative field, such as nerves. One application for retractors is for pulling the spinal cord out of the way during operations on the spinal column (spinal cord). While the spinal cord can be pulled gently out of way so that the surgeon has access to the anterior portions of the spine, it is possible to cause great harm to the spinal cord by improperly using a retractor by applying too much pressure to the cord or over too long a period of time.

The human spine is composed of a column of thirty-three bones, termed vertebrae, and their joining structures. The twenty-four vertebrae nearest the head are separate bones capable of individual movement and are generally connected by anterior and posterior longitudinal ligaments and by discs of fibrocartilage, material termed intervertebral discs, positioned between opposing faces of adjacent vertebral bodies. The remaining nine vertebrae are fused to form the sacrum and the coccyx and are incapable of individual movement. The vertebral body and the dorsal vertebral arch of each of the twenty-four mobile presacral vertebrae enclose an opening termed the vertebral foramen, through which the spinal cord, a column of nerve tissue which communicates nerve impulses between the brain and the rest of the body, and spinal nerve roots pass and are protected from damage.

The intervertebral discs are sometimes damaged by local pressure on the spinal cord or excessive bending of the spinal cord which can result in disorders associated with blockage of the nerve impulses traveling along the spinal cord, in turn producing pain, paresthesia, or loss of motor control which must be resolved by removing the causative condition. Also, herniation of the intervertebral disc can occur, in which a small amount of tissue protrudes from the sides of the disc into the foramen to compress the spinal cord. Another common condition involves the development of small bone spurs, termed osteophytes along the posterior surface of the vertebral body, again impinging on the spinal cord.

Surgery is often times required to correct the above and other problems. In one procedure, the involved vertebral bodies are exposed and the intervertebral disc is removed or replaced. During the surgical procedure the spinal cord must be retracted so that the interior of the vertebral foramen is exposed. This retraction is carried out by a surgical assistant or by the surgeon, himself or herself, with one hand while operating with the second hand. The retractor typically used for spinal cord retraction consists of a curved bill capable of pulling the spinal cord, where such bill is connected to a handle. Quite often, the spinal cord is retracted to the extent necessary to expose the area on which it is desired to operate, without proper attention being paid to the pressure or force exerted on the cord. Excessive retraction of the spinal cord can cause severe damage to the spinal cord. Using a conventional retractor, the user has no way of knowing if he or she is applying a prescribed amount of force or too much force on the spinal cord or if force is applied for too long a time.

In the U. S. Pat. No. 4,784,150 to Voorhies et al., the inventors disclose the use of a test embodiment of the retractor having a strain gauge attached thereto. The gauge is attached to the retractor to measure the pressure applied by the retractor while the inventors were simultaneously measuring the blood flow with an infrared device. The inventors further discuss other experiments carried out by other scientists wherein strain gauges attached to retractors were used.

SUMMARY OF THE INVENTION

Briefly described, the present invention involves a protector retractor (retractor) designed to safely retract or otherwise manipulate a spinal cord. The retractor includes a head or bill with a sidewise, U-shaped, curvilinear, contact surface having a sensor forming the inner surface. The sensor, when in use, detects any pressure on the spinal cord, exerted by the retractor bill, and is electronically connected, through a microcomputer, to an operator readable display of various parameters of the operating retractor.

Accordingly, it is an object of the present invention to provide a retractor which enhances the control available to the retractor operator.

Another object of the present invention is to provide a retractor which is capable of indicating, visually, the pressure applied, the elapsed time of the pressure application and providing an audible signal for indicating when the pressure has been applied for a dangerous length of time.

Another object of the present invention is to provide a protector retractor which is inexpensive to manufacture, durable in structure and efficient in operation.

Another object of the present invention is to provide a process for safely and effectively moving and holding body tissue in a displaced position.

Another object of the present invention is to provide an apparatus and process which will temporarily move and hold body tissue in a displaced or deformed condition while simultaneously monitoring both the amount of force applied to this tissue and the time lapse over which such force is applied while providing alarms when either a prescribed force limit or prescribed time limit is exceeded.

Another object of the present invention is to provide a retractor which is safe to use and is less likely to cause damage to the spinal cord.

Other objects, features, and advantages of the present invention will become apparent from the following description when considered in conjunction with the accompanying drawings wherein like characters of reference designate corresponding parts throughout the several views.

DETAILED DESCRIPTION OF THE PREFERRED EMBODIMENT

Figure 1:
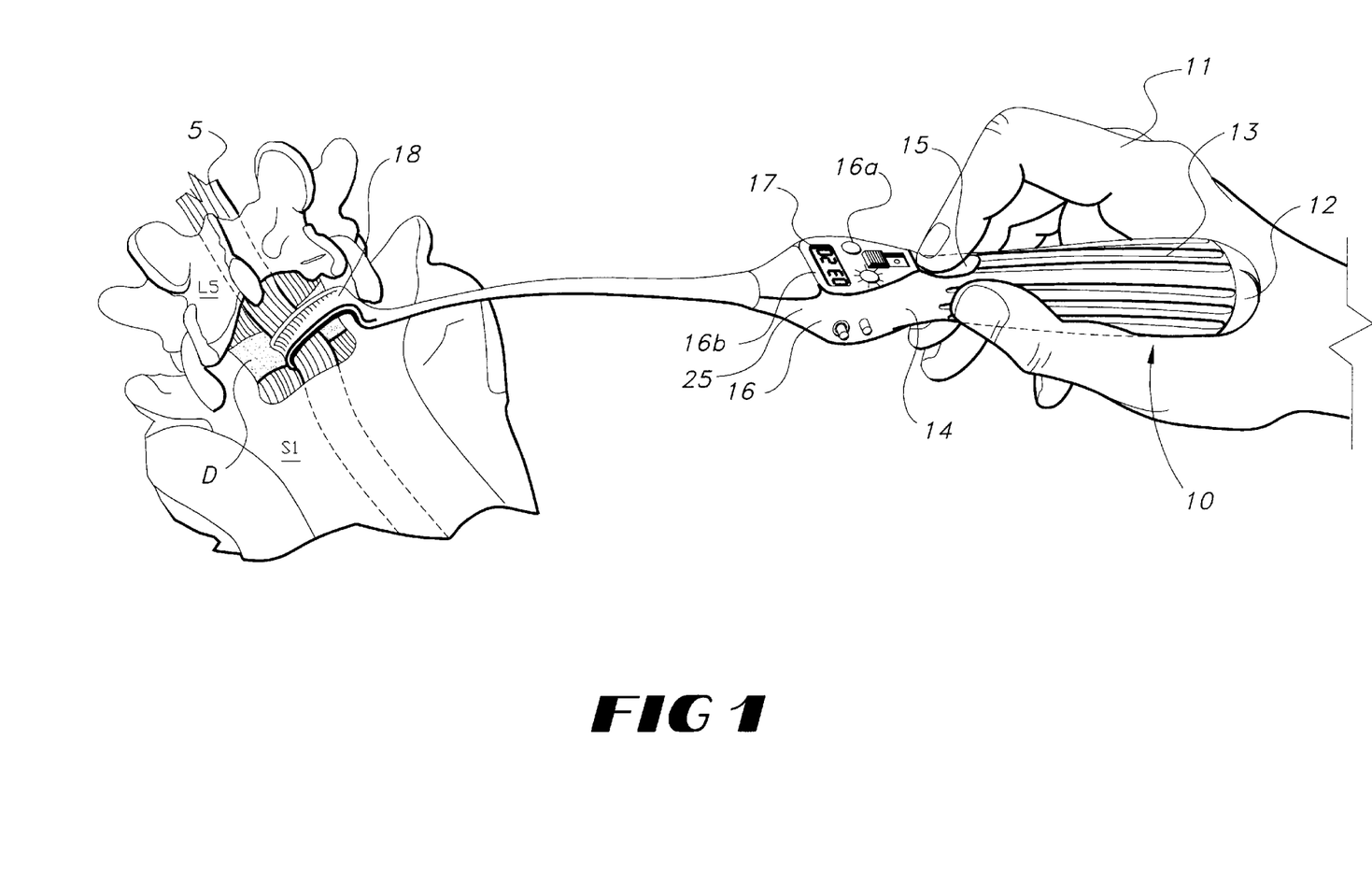
FIG. 1 is a perspective view of the retractor of the present invention in use retracting a portion of the spinal cord adjacent to a disc between vertebrae L5 and S1.
Figure 2A:
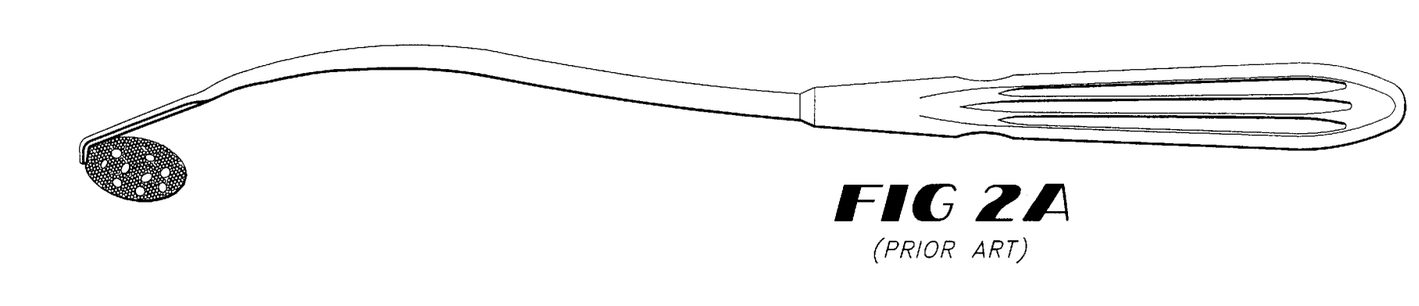
FIG. 2A is a side elevational view of a retractor of the prior art.
Figure 2B:
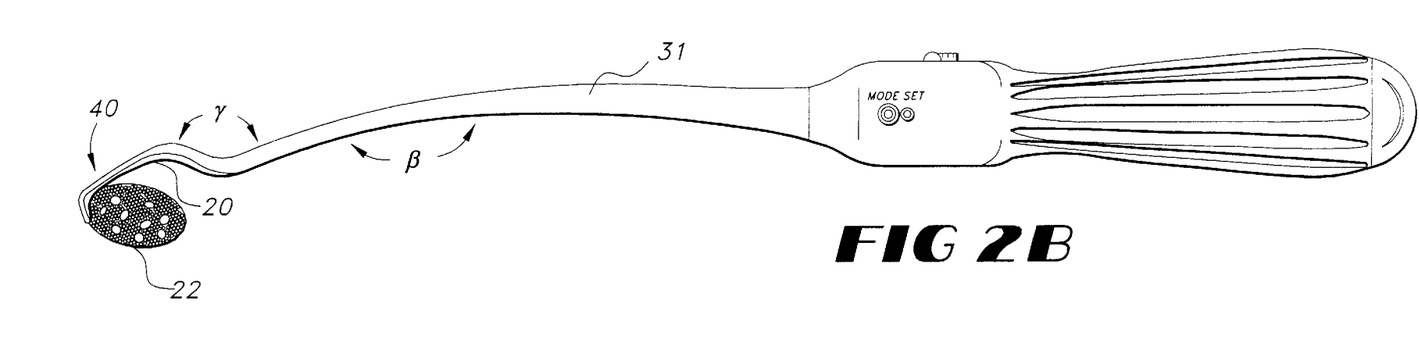
FIG. 2B is a side elevational view of a retractor shown in FIG. 1.
Figure 4:
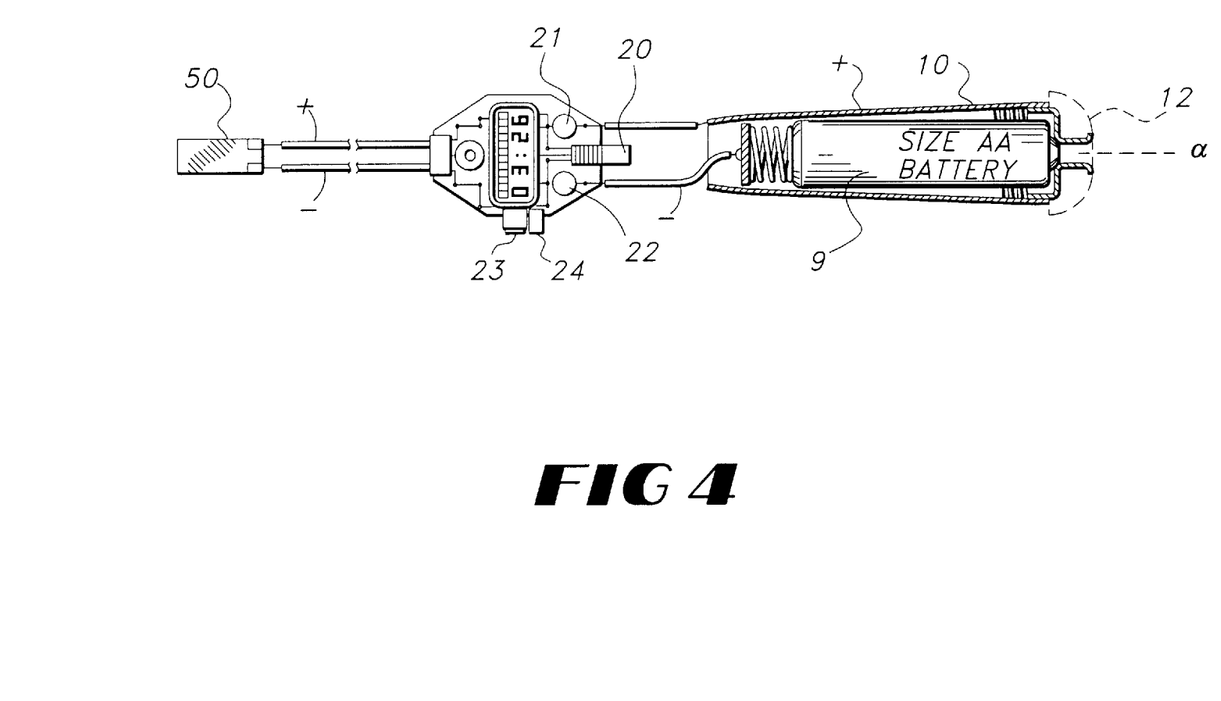
FIG. 4 is a fragmentary schematic view of certain electrical components of the retractor shown in FIG. 1.

Referring now in detail to the embodiment chosen for the purpose of illustrating the preferred embodiment of the present invention, numeral 10 denotes generally the handle of the retractor of the embodiment. In FIG. 1 this handle 10 is shown being gripped in the right hand 11 of an operator who is using the retractor to pull to one side a portion of a spinal cord S adjacent to a disc D between vertebrae L5 and S1. As more specifically shown in FIG. 4, handle 10 is essentially a tubular member having an axis α, the interior of handle 10 carrying a dry cell battery 9. The upper end of the handle 10 is closed by a removable cap 12, the shaft 12a of which is externally threaded and is threadedly received in the open upper end of handle 10 for confining battery 9 within handle 10.

The exterior of handle 10 is generally cylindrical and tapers forwardly. The exterior surface of handle 10 is provided with a plurality of axially or longitudinally extending ridges 13 which are arranged in circumferentially spaced relationship around the handle 10. Ridges 13 form a grip for handle 10. Handle 10 tapers toward and merges into a narrowed neck 14.

One side of the portion of the handle 10 adjacent to neck 14 is a flat, slightly concaved surface which forms a finger rest 15 which is shown receiving the index finger of hand 11.

Figures 5, 6, 7:
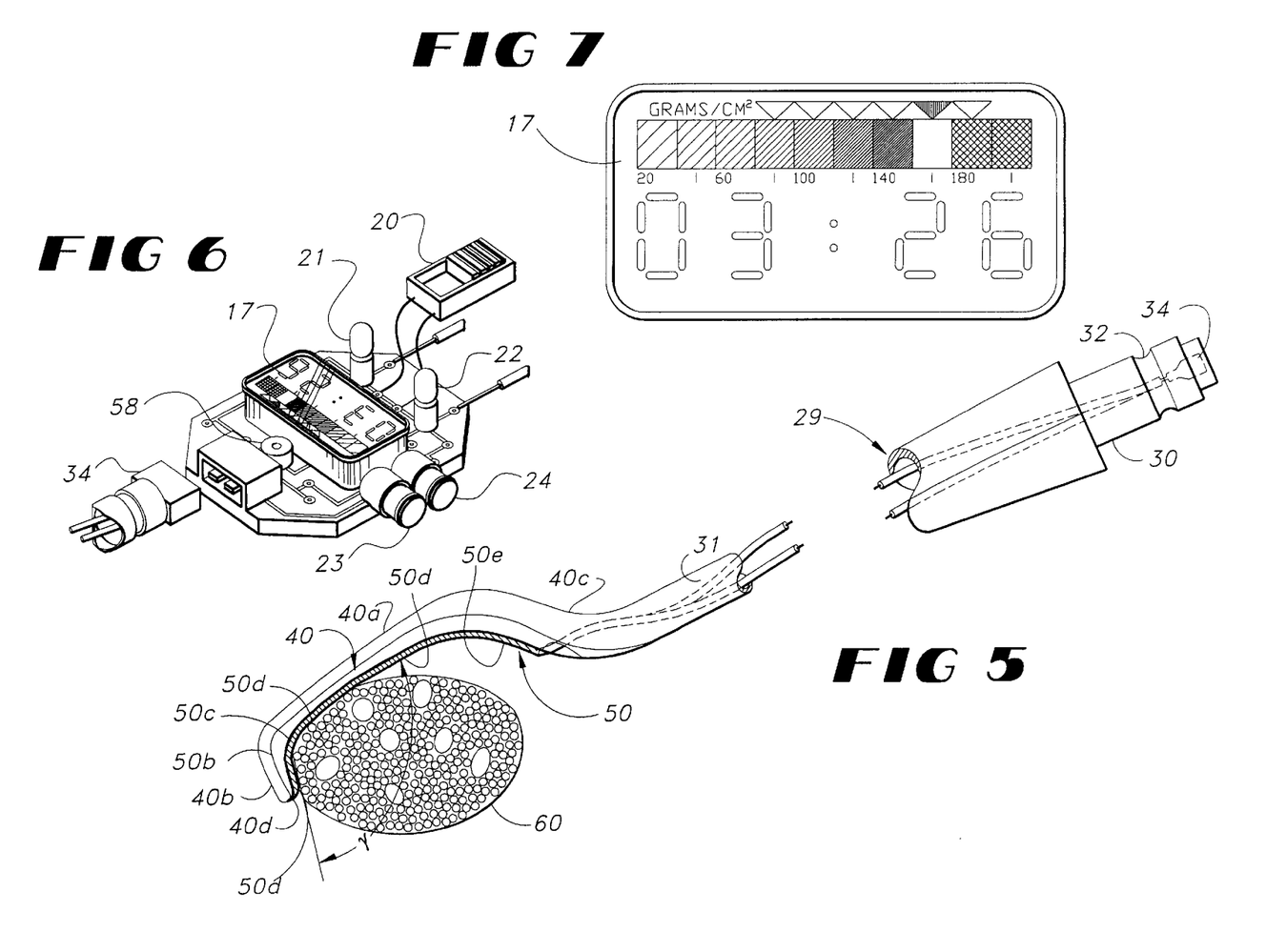
FIG. 5 is an enlarged perspective, partially cut away, view of the retractor of the present invention showing a portion of the sensor engaging the spinal cord.
FIG. 6 is an enlarged fragmentary perspective schematic wiring diagram of certain electrical components of the retractor shown in FIG. 1.
FIG. 7 is an enlarged plan view of the display of a retractor shown in FIG. 1, showing a typical screen.

From neck 14, the handle 10 progressively widens to a substantially rectangular housing 16 having a hollow interior and an upper surface 16a with a rectangular display window 16b therein. This display window 16b surrounds an indicating member such as LCD display 17 which provides a visual display of the force applied and a "time elapsed" read out thereon and provides other display information in the form of indicia. In FIG. 7 the indicia shows a time lapse of 3 minutes and 26 seconds. It also shows a strain of force of about 130 grams/cm².

Also in the surface 16a is an "on-off" switch 20, a red LED pressure limit light 21 and a green LED time limit light 22. At the side of housing 16 is a mode selection switch 23 and a multi-function switch 24 to selectively provide the following functions: "reset time", "battery test", "adjust and set pressure limit", and "set time limit". Each function has an associated screen portion on the display 17.

From the central housing 16, a hollow nose 25 tapers forwardly to terminate in a flat end 26 containing a round socket 27 with a spring loaded ball (not shown) in the socket.

Figure 3:
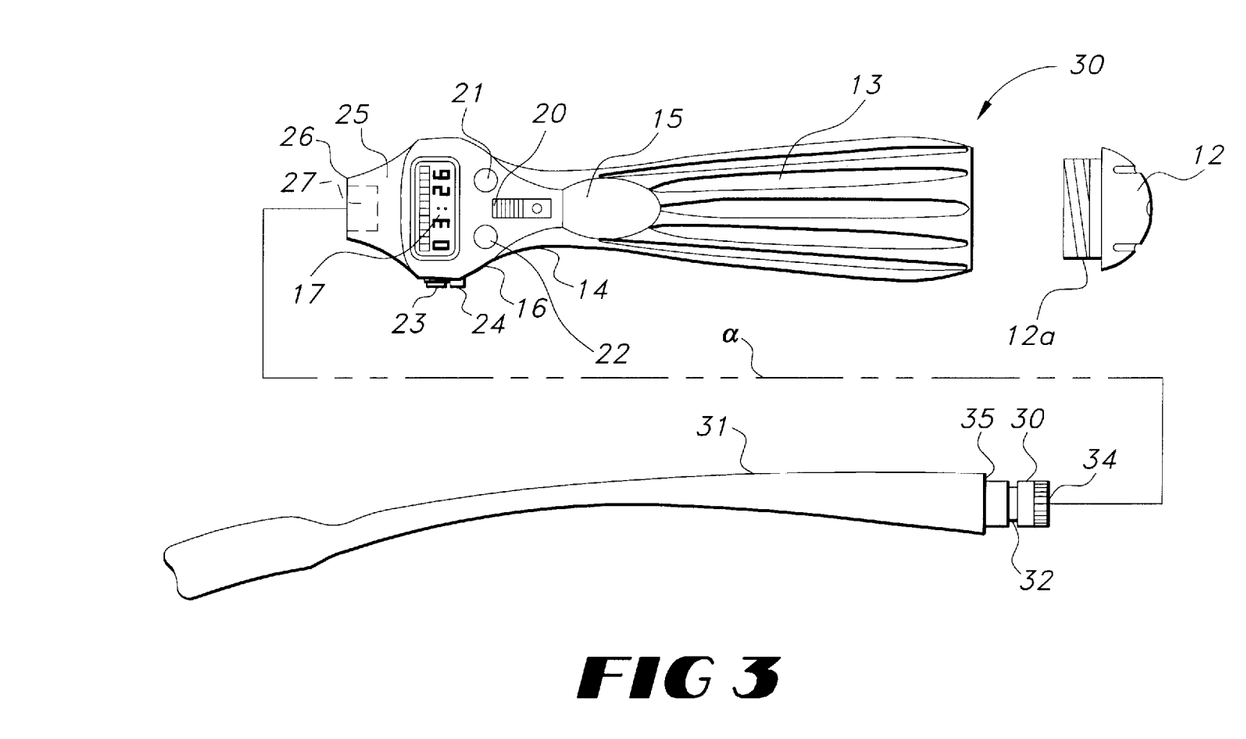
FIG. 3 is an enlarged, exploded, plan view of the retractor shown in FIG. 1.

The bill portion 29 includes a plug 30, seen in FIG. 3 and FIG. 5, for example, on the proximal end of a slightly arcuate retractor staff or stem 31. Plug 30 has an annular groove 32, best seen in FIG. 5, the groove 32 cooperating with the yieldable ball (not shown) in nose 25, which snaps into the groove 32, and forms a detent to assure that the plug 30 is and remains fully seated in socket 27. When plug 30 is seated, electrical spades 34 of the plug 30 are received in electrical terminals (not shown) of the socket 27.

The narrow, but quite strong, arcuate, elongated staff or stem 31 extends away from nose 25, supporting at its distal end a sidewise opening head or bill 40.

As shown in FIG. 5, bill 40 is shaped like a curved, flattened head of a spoon, to provide a relatively long and generally flat base 40a, joined to an abruptly bent, relatively short, straight, outer tip or distal leg portion 40b, which diverges from the distal end of base 40a, at between about a 100° to about a 120° obtuse angle γ.

The inner or proximal leg portion 40c, which integrally joins the distal end of staff 31 and the proximal end of base 40a is disposed at an obtuse angle of between about 120° to about 160° with respect to base 40a and merges into the distal end of staff 31, such that the base 40a is offset from the distal end portion of narrow distal portion of staff 31.

According to the present invention, the inner surface of the U-shaped bill 40 has, adhered thereto, a thin foamed rubber or synthetic rubber cushion or liner 41 which, in turn, carries, adhered thereto, a generally rectangular, flexible, deformable, generally flat, thin, impact sensor or hydrostatic sensor or strain gauge 50 which is bent to conform to the contour of the cushion 41 and the surface of the head 40 which forms a sidewise opening bill 40. The sensor or strain gauge 50 terminates in a rounded convex tip 50a conforming to and in alignment with the convex tip 40d of bill 40. The strain gauge 50 comprises a generally flat, inwardly extending, distal portion which overlies the flat leg portion 40b of bill 40. Thereafter, the strain gauge 50 curves inwardly about a transverse axis forming an obtuse angle which is approximately equal to angle γ. An intermediate portion of strain gauge 50 forms a generally flat, slightly concaved base 50c which overlies the base 40a of bill 40. Thence, the strain gauge 50 is bent again at an obtuse angle, providing a proximal portion 50d, overlaying inner arm 40c. The leg portion 50b, base 50c and proximal portion 50d define a continuous, transversely flat contact surface of strain gauge 50.

The strain gauge or sensor 50 comprises a piezoelectric sensor that produces a detectable signal output when force is applied thereto. The voltage or bias of the signal output is proportional to the force applied, with greater force resulting in higher voltage.

Figure 8:
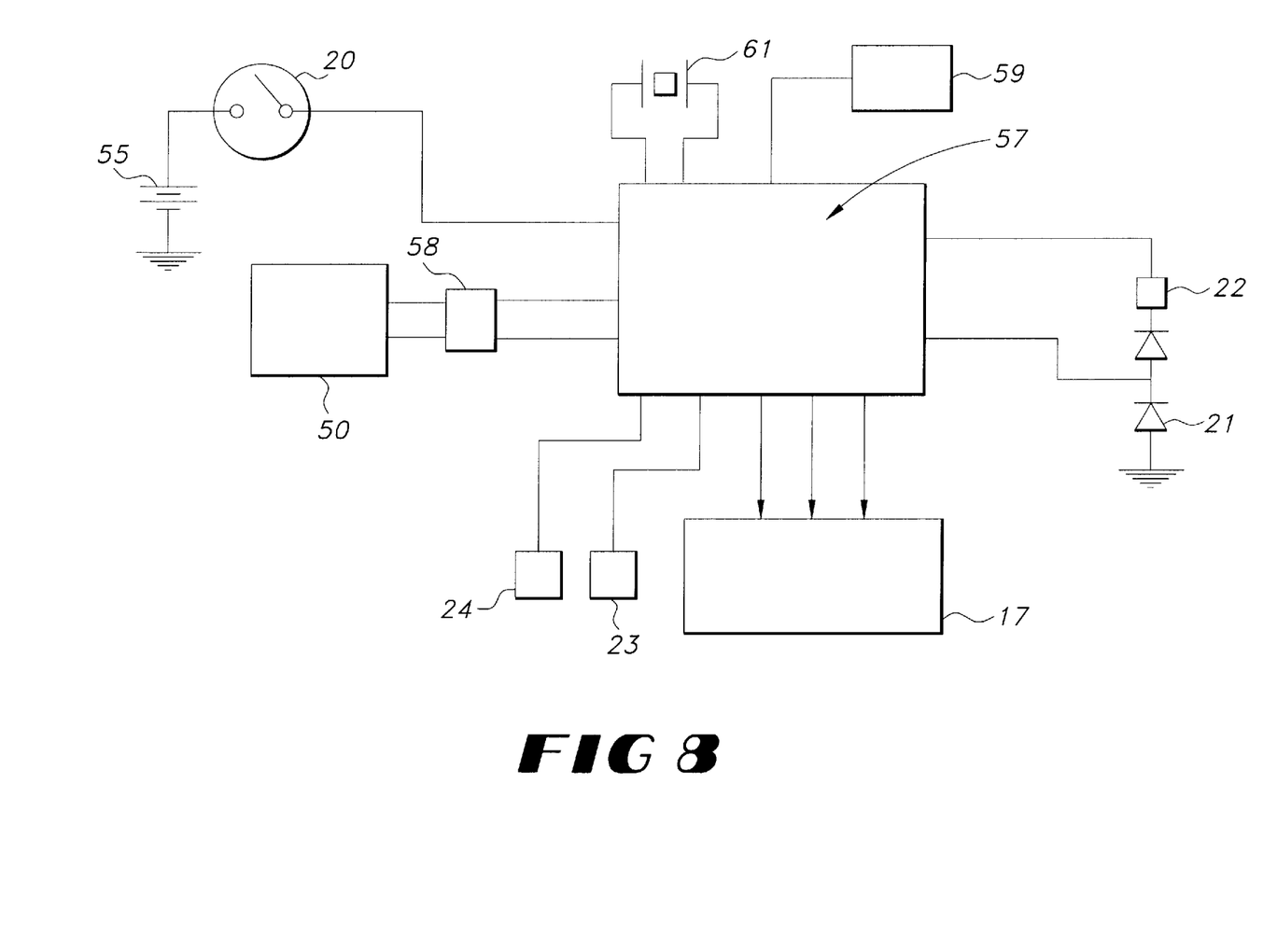
FIG. 8 is a schematic wiring diagram of the circuitry of the retractor shown in FIG. 1.

As best seen in FIG. 6 and FIG. 8, the battery 9 supplies current, via switch 20 to a microcomputer 57 which, when properly programmed, supplies appropriate signals for screens for the display 17. The sensor 50 is connected through an A/D converter 58 to the microcomputer 57, so as to supply digital signals to the microcomputer which are indicative of the total pressure applied to the surface of the sensor 50. A clock signal from clock 61 is provided to the microcomputer 57 and the alarm device 59 is connected to and actuated by the microcomputer 57 when more than a prescribed pressure is applied to the tissue of a person's body by bill 40.

The inner contact surface of leg portion 50b, base 50c and proximal portion 50d of strain gauge 50 carried by bill 40 is used to extend partially around and grasp increments of spinal cord S and retract sidewise a portion of the spinal cord S, as shown in FIGS. 1 and 5.

The gauge or sensor 50 is mounted so that it covers the entire contact surface of the head or bill 40 and will be deformed if any portion of the contact surface of sensor 50 contacts the spinal cord S. Thus, any force applied by the contact surface sidewise and/or axially of handle 10 against spinal cord S generates a signal indicative of this force applied by the contact surface.

As shown or interior of FIG. 5, power to operate the microcomputer 57 is a typical dry cell battery 9 which is inserted into a cavity or interior of the handle 10. The device can also be adapted to be operated using an AC power source.

The green LED light 22, when lighted, indicates when a previously set time limit has expired; and a red LED 24 light, when lighted, indicates when a previously set pressure limit has been achieved. The microcomputer 57, which controls the screen presented on the display 17 and the sensor 50, is turned on and off by switch 20 which is conveniently adjacent to the index finger of hand 11 when the retractor is held. The display 17 further includes an audible alarm 59 which can be set to indicate when either the pressure limit or the time limit has been reached. The display 17 can display selected screens or parameters. The mode select button 23 is for selecting whether the pressure or the time shall be displayed on display 17 and a reset button 24 functions to test the battery and can be used to adjust and set new and different pressure and time limits.

The retractor is designed so that different retractor bill portions 29 can be attached to the handle portion 10. In this way, various sizes and shapes of bills or heads, such as bill 40, can be used with the handle portion 10 and its display 17.

In operation, after appropriate limits have been installed for time and pressure applied by the sensor 50, the retractor is held in the hand 11, the switch 20 is turned on and the retractor is manipulated to dispose the sensor 50 adjacent to a portion of spinal cord S. The protector retractor is then progressively moved sidewise into engagement to partially encircle an increment of an intermediate portion of the spinal cord. The retractor is then manipulated to move the contacted portion of the spinal cord S sidewise. The display 17 continuously indicates the time elapsed and the intensity of the force or pressure applied. The audible alarm 59 indicates when a prescribed time has elapsed and also if a prescribed force or pressure has been exceeded. The U-shape of the sensor 50 enables it to be used for pushing (protractive) as well as pulling the spinal cord.

It will be obvious to those skilled in the art that many variations may be made to the embodiment of the invention disclosed herein, without departing from the scope thereof as defined by the appended claims.

What is claimed is:

1. A surgical retractor, comprising:
    (a) a handle portion including a grip by which the retractor is manipulated;
    (b) a staff attached to said handle portion and having a distal end;
    (c) a head on said distal end, said head having a contoured surface;
    (d) a piezoelectric sensor carried by said contoured surface of said head, said sensor generating signals;
    (e) a microcomputer electrically connected to said sensor, said microcomputer including means for selectively programming said microcomputer;
    (f) at least one visual display communicating with said microcomputer to provide displays indicative of the signals from said sensor; and
    (g) an audible alarm communicating with said microcomputer to provide an audible response indicative of the signals from said sensor.

2. The surgical retractor of claim 1, wherein said staff is removably carried by said handle.

3. The surgical retractor of claim 1, wherein said sensor is generally U-shaped.

4. The surgical retractor of claim 1, wherein said sensor is a strain gauge.

5. The surgical retractor of claim 1, including a clock for generating signals indicating the time that pressure has been applied to said sensor.

6. The surgical retractor of claim 1 wherein said audible alarm is adapted to indicate when a preset pressure limit has been achieved.

7. The surgical retractor of claim 1, wherein said at least one visual display comprises a force display.

8. The surgical retractor of claim 7, wherein said at least one visual display further comprises an elapsed time display.

9. The surgical retractor of claim 8, wherein said at least one visual display further comprises a light indicative of a preset pressure limit.

10. The surgical retractor of claim 7, wherein said at least one visual display further comprises a light indicative of a preset time limit.

11. A surgical retractor used by an operator for applying a force to tissue in the body of a person during a surgical procedure, comprising:
    (a) a handle for being held by the operator externally of the body;
    (b) an elongate staff removably carried by said handle, said staff having a proximal and a distal portion including a head remote from said proximal portion, said proximal portion being connected to said handle so that it may be manipulated by manipulation of said handle;
    (c) a sensor carried on the head of said staff and being capable of delivering a signal;
    (d) a visual indicating member positioned on said handle, said indicating member being constructed and arranged to receive the signal from said sensor to display the amount of force applied to the tissue by the head of said staff; and
    (e) an alarm carried by the handle to audibly indicate when a predetermined amount of force is exceeded.

12. The surgical retractor as claimed in claim 11 wherein said sensor is a strain gauge.

13. The surgical retractor as claimed in claim 11, wherein said indicating member includes an elapsed time display.

14. The surgical retractor as claimed in claim 11, further comprising a timer adapted to receive the signal from said sensor to indicate the amount of time the force is applied to the tissue by said retractor.

15. A surgical retractor suitable for retracting and protracting body tissue, said retractor comprising
    (a) a handle portion with a grip by which the retractor may be manipulated by a person;
    (b) a portable electrical power source within said handle portion;
    (c) a retractor staff operably connected to said handle portion and extending through an intermediate portion to a generally U-shaped distal end having an inner face and an outer face,
        (i) said intermediate stem portion configured in an arcuate shape and arranged in a plane,
        (ii) said distal end having a reverse bend portion from the end of said stem,
        (iii) a flat let leg portion, and
        (iv) a short distal leg portion extending from said flat leg portion at an obtuse angle of from 100 to about 120 degrees.

16. The surgical retractor according to claim 15, wherein said distal end lies in said plane, and said distal end along said inner face includes a first cushion layer formed of a rubber-like material, and a thin, continuous deformable layer of a sensor responsive material, such as a piezoelectric sensor.

17. The surgical retractor according to claim 16, wherein said handle portion includes a microcomputer and a digital display unit arranged to receive and translate signals from said sensor material, which signals are in proportion to the force applied to said sensor responsive material.

18. The surgical retractor according to claim 17, wherein said digital display unit includes an alarm device activated by a pre-set pressure limit that may be applied to said body tissue through said sensor responsive material.

19. The surgical retractor according to claim 17, wherein said microcomputer and digital display unit includes an audio alarm system activated by a pre-set time limit to avoid prolonged contact with said body tissue.

20. The surgical retractor according to claim 15, wherein said retractable staff is removably and electrically attached to said handle portion.

\* \* \* \* \*